US009329132B2

(12) United States Patent
Rogers et al.

(10) Patent No.: US 9,329,132 B2
(45) Date of Patent: May 3, 2016

(54) METHOD TO INCREASE THE NUMBER OF DETECTABLE PHOTONS DURING THE IMAGING OF A BIOLOGICAL MARKER

(75) Inventors: Kelly Rogers, Victoria (AU); Spencer Shorte, Paris (FR); Joseph Dragavon, Paris (FR); Samantha Blazquez, Lons (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 13/637,551

(22) PCT Filed: Mar. 25, 2011

(86) PCT No.: PCT/IB2011/051282
§ 371 (c)(1),
(2), (4) Date: Dec. 17, 2012

(87) PCT Pub. No.: WO2011/117847
PCT Pub. Date: Sep. 29, 2011

(65) Prior Publication Data
US 2013/0115647 A1     May 9, 2013

(30) Foreign Application Priority Data
Mar. 26, 2010 (EP) ..................................... 10290158

(51) Int. Cl.
*G01N 21/64*     (2006.01)
*B82Y 15/00*     (2011.01)
(52) U.S. Cl.
CPC ............ *G01N 21/6486* (2013.01); *B82Y 15/00* (2013.01); *G01N 21/6428* (2013.01); *G01N 2201/06193* (2013.01)
(58) Field of Classification Search
None
See application file for complete search history.

(56) References Cited

U.S. PATENT DOCUMENTS

2008/0213377 A1 *   9/2008   Bhatia et al. .................. 424/489

OTHER PUBLICATIONS

Maysinger, Dusica; et al; "Real-Time Imaging of Astrocyte Response to Quantum Dots: In Vivo Screening Model System for Biocompatibility of Nanoparticles" Nano Letters, 7, 2513-2520, 2007.*
Leevy, W. Matthew; et al; "Optical imaging of bacterial infection Models" Drug Discovery Today: Disease Models, 4, 91-97, 2007.*
Welsher, Kevin; et al; "Selective Probing and Imaging of Cells with Single Walled Carbon Nanotubes as Near-Infrared Fluorescent Molecules" Nano Letters, 8, 586-590, 2008.*
Kim, Sungjee; et al; "Near-infrared fluorescent type II quantum dots for sentinel lymph node mapping" Nature Biotechnology, 22, 93-97, 2004.*
International Search Report/Written Opinion for Application No. PCT/IB2011/051282 dated Nov. 2, 2011.
Amiot, C. L. et al., *Near-Infrared Fluorescent Materials for Sensing of Biological Targets*, Sensors, MDPI vol. 8, (2008) 3082-3105.
Bakalova, R. et al., *Quantum Dots Versus Organic Fluorophores In Fluorescent Deep-Tissue Imaging—Merits and Demerits*, General Physiology and Biophysics vol. 27, No. 1, (2008) 231-242.
Conte, J. C. et al., *Radiative Energy Transfer I. General Equations*, Journal of Luminescence vol. 22, No. 3, (1981) 273-284.
Deliolanis, N. C. et al., *Performance of the Red-Shifted Fluorescent Proteins in Deep-Tissue Molecular Imaging Applications*, Journal of Biomedical Optics, SPIE—International Society for Optical Engineering vol. 13, No. 1, (2008) 44008-1-9.
Jiang et al., *Assessing Near-Infrared Quantum Dots for Deep Tissue, Organ, and Animal Imaging Applications*, Journal of the Association for Laboratory Automation vol. 13, No. 1, (2008) 6-12.
Wang, Y, et al., *Bioapplication of Nanosemiconductors*, Materials Today vol. 8, No. 1, (2005) 20-31.

* cited by examiner

*Primary Examiner* — Renee Claytor
*Assistant Examiner* — David Berke-Schlessel
(74) *Attorney, Agent, or Firm* — Alston & Bird LLP

(57) ABSTRACT

The present invention relates a method to determine the presence of a photon producing biological marker in a cell, tissue or organism of interest. The method is based on Fluorescence by Unbound Excitation from Luminescence (FUEL) and comprises the steps of a) providing conditions suitable for the biological marker to produce at least one first photon by luminescence; b) providing a FUEL probe pair-upper (FPP-U) disposed in proximity to the cell, tissue or organism, wherein the at least one first photon of step a) excites the FPP-U, which emits at least one second photon. The FPP-U may be selected from the group of quantum dots, carbon nanotubes, fluorescent proteins, diamond nanocrystals and metalloporphyrins. This method is characterized in that said biological marker and said FPP-U are not bound and in that each of the at least one second photon(s) are of a longer wavelength than each of the at least one first photon(s).

12 Claims, 11 Drawing Sheets

METHOD TO INCREASE THE NUMBER OF DETECTABLE PHOTONS DURING THE IMAGING OF A BIOLOGICAL MARKER

FIELD

The present invention relates to a new method to red shift an optical signal from a biological marker. In particular the present invention relates to an excitation mechanism between a luminescent biological marker and a fluorophore. The present patent application also relates to kits for implementing a method according to the present invention and the use of an unbound fluorophore to produce a photon which is red shifted in comparison to a photon produced by a biological marker.

BACKGROUND

The use of biological markers which produce an optical signal has revolutionized several aspects of the life sciences and in particular has allowed for the real time observation of in vivo phenomenon such as endocytosis, embryonic development, infection, tumor development and calcium signaling. Increasingly these same technologies are also being used to visualize more and more biological and pharmaceutical processes in situ within a target cell, isolated tissue or whole organism.

There are essentially three mechanisms for generating a light emission based optical signal using a biological marker:
1. Bioluminescence.
2. Chemiluminescence.
3. Fluorescence.

Bioluminescence is the production and emission of light by a living organism or a fragment thereof such as an enzyme. Bioluminescence is a naturally occurring form of chemiluminescence (see below), where energy is released by a chemical reaction in the form of light emission. Adenosine triphosphate (ATP) is involved in most bioluminescent reactions and therefore generally bioluminescent reactions occur in vivo.

Chemiluminescence is the emission of light as the result of a chemical reaction. This is different to bioluminescence as the components of the chemical reaction do not necessarily occur in vivo.

Fluorescence is the emission of light by a substance that has absorbed radiation of a different wavelength. In most cases, absorption of light of a certain wavelength induces the emission of light with a longer wavelength. The fluorescent molecule is generally called a fluorophore and no chemical reaction is involved in the emission of light following excitation.

To take the example of bioluminescence, the use of organisms that have been genetically modified with genes encoding bioluminescent probes such as aequorin or various luciferases allows for the non-invasive visualization of many biological processes within living organisms and small animal models (1-3). Bioluminescence imaging is highly sensitive because signals can be optically detected within intact organisms, such as mice, due to the very low levels of intrinsic bioluminescence of mammalian tissues (4). Bioluminescent probes such as aequorin (5, 6) or the enzyme luciferase (bacteria, firefly, *Cypridina* (7) or *Renilla* (8)) have been incorporated into host cells or pathogens for bioluminescent imaging. These tools have been applied to studies ranging from infection and tumor development to calcium signaling. However, most of these biological markers emit light in the blue-green-yellow (400-650 nm) region of the color spectrum (9), which overlaps with the major absorption spectra of mammalian tissues and, in particular, with the absorption spectra of oxy-haemoglobin, de-oxyhaemoglobin and melanin, thus decreasing the efficacy of the detection (1, 10). Due to the presence of these absorbers, a major challenge in in vivo optical imaging is to achieve higher levels of sensitivity by developing optical probes emitting light in the red to near infrared (NIR) spectrum (650-900 nm), which is only weakly absorbed in living mammalian tissues.

Even with these drawbacks the use of this technology has readily applied itself to experiments involving models such as small rodents both anaesthetized and non-anaesthetized/ freely moving (21). As indicated above in small rodent models (and more generally in mammals), the presence of various haemoglobins and tissues which readily absorb in the blue-yellow region of the color spectrum, reduces the ability to excite and detect fluorophores, or to monitor the luminescent signal produced by modified cells and bacteria if this is in this same spectrum.

Significant effort to improve the number of detectable photons from a bioluminescent source has led to the development of a vast array of new and/or improved bioluminescent probes and techniques that increase the number of emitted photons in the red region of the color spectrum (>650 nm). It has not proven too difficult to design fluorophores or fluorescent proteins that are both excited and emit in the red—near infrared (NIR) (22).

However, to achieve a similar red-shift for the bioluminescent emission has proven to be more difficult. One method towards establishing the desired red-shift has been to develop luciferase variants that are capable of emitting in this part of the red-NIR part of the light spectrum. However, most of the mutants/mutations developed so far have led to emissions in the yellow-green region (9) and there have been only a few examples of successful red bioluminescent production (11), and such red-NIR engineered proteins generally produce significantly less signal than the unengineered yellow-green versions.

Given the difficulty in producing red-NIR bioluminescence, significant effort has therefore been put towards creating applicable methodologies to produce a red-shift in the emitted photons using bioluminescence resonance energy transfer (BRET) (13). Several groups have already demonstrated the success of this technique utilizing luciferases bound to QDs (8) or other fluorophores (7) with large Stokes shifts.

In these previous methods, workers have investigated BRET by conjugating an eight-mutation variant of *Renilla reniformis* to a quantum dot, with the *R. reniformis* acting as the energy donor and quantum dots (QDs) as the energy acceptor thus achieving an emission peak at 655 nm from the QD following energy transfer (8). More recently, a biotinylated *Cypridina* luciferase was conjugated to a far-red fluorescent indocyanine derivative, providing an emission peak at 675 nm (7). However, in BRET, the donor and acceptor must be in close proximity (less than 10 nm (12-15)) as it involves a non-radiative energy transfer from the luminescent donor to the acceptor.

The use of BRET has been highly successful but can be difficult to implement since various synthetic techniques must be utilized in order to conjugate the donor luciferases to the acceptor QD or other fluorophore to achieve the desired resonance energy transfer. The need to bind the biological marker to a QD or other 'red' photon emitting acceptor, may make the biological marker less efficient as a means of visualizing 'in vivo' a cell, tissue or organism. This can be the result of interference with the function or ability of biological marker to produce a signal and/or move freely so as to associate with its target, where appropriate.

SUMMARY

In this patent application, the inventors present an alternative to resonance energy transfer (RET) that does not require the donor and acceptor sources to be in close molecular proximity yet is still capable of providing the desired red-shift in the photons emitted from the biological marker. This phenomenon, termed Fluorescence by Unbound Excitation from Luminescence (FUEL), is distinct from RET because the donor and acceptor do not need to be in molecular proximity and FUEL can occur over substantially larger distances (micron(s) or further).

According to a first aspect of the present invention there is provided a method to determine the presence of a photon producing biological marker in a cell, tissue or organism of interest comprising the steps:

a) providing conditions suitable for the FPP-L to produce at least one first photon;

b) providing a FPP-U disposed in proximity to said cell, tissue or organism, wherein said at least one first photon of step a) excites said FPP-U, which emits at least one second photon;

said method being characterized in that said FPP-L and said FPP-U are not bound and in that each of said at least one second photon (s) are of lower energy than each of said at least one first photon (s).

FUEL involves the use of a FUEL probe pair (FPP) which consists of two components: the FPP-lower (FPP-L) and the FPP-upper (FPP-U), either of which could be the biological marker.

For instance, an RFP-tagged parasite could be introduced to susceptible GFP-tagged cells and cell infection studied. In this case an FPP-L, such as a QD, is also present in the system being studied which emits photons that excite RFP leading to the emission of further photons from the RFP that can be detected. Therefore the biological marker is the tagged parasite but this is also the FPP-U.

Alternatively the GFP-tagged cells could be the FPP-L provided with conditions that cause it to emit photons, such as an internal or external source of excitant light, these GFP photons then excite the FPP-U disposed in proximity to the cells, wherein the photons from the FPP-U are then detected.

In both instances the presence of a biological marker is detected using FUEL.

The FPP-L may be the luminescent biological marker, this biological marker can be, but is not limited to, a bioluminescent, chemiluminescent or fluorophores/fluorescent probes including fluorescent proteins. The FPP-U is also a luminescent molecule that may be, but is not limited to, fluorophores/fluorescent probes including quantum dots, fluorescent proteins, carbon nanotubes, nanodiamonds or metalloporphyrins.

It is necessary for the emission spectrum of the FPP-L to overlap with the excitation spectrum of the FPP-U to ensure an adequate production of red-shifted photons.

In accordance with a further aspect of the present invention a plurality of intermediary FFPs may be interposed in a cascade of photon excitation and emission between the biological marker and the final FPP-U which produces the observed photon. In particular therefore the present invention relates to a set of FPPs each of which has an excitation spectrum which overlaps with the emission spectrum of the previous member in the cascade and in turn produces a photon which is within the excitation spectrum of the next member in the cascade.

According to this aspect of the invention there is provided a 'cascade' method to determine the presence of a photon producing luminescent biological marker in a cell, tissue or organism of interest comprising the steps:

a) providing conditions suitable for a first FPP to produce at least one first photon;

b) providing a second FPP disposed in proximity to said cell, tissue or organism, wherein said at least one first photon of step a) excites said second FPP, which emits at least one second photon;

wherein step b) is repeated at least one further time, wherein for each additional step a further FPP disposed in proximity to said cell, tissue or organism, other than said first or second FPP, wherein said further FPP is specifically excited by the at least one photon emitted in the previous step and in turns emits at least further photon;

wherein in a final step said further photon is detected;

said method being characterized in that said plurality of FPPs are not bound and in that each of said at least one photon (s) are of a longer wavelength than each of said at least one photon (s) from the previous step.

In a preferred embodiment of this method wherein said biological marker is either said first or said second FPP.

Any of the specific features detailed herein relating to the properties of the FPP-Ls or FPP-Us are applicable to the plurality of FPP used in this 'cascade' method.

This method concerns the use of FPP-Us that are sufficiently excited by photons emitted by a biological marker, such as a bioluminescent bacteria, as a means to enhance the non-invasive detection of the biological marker in vivo. Quantum dots are nanocrystals (10-40 nm in size) consisting of a semiconductor core material (e.g., CdSe) and an amphiphilic polymer coating covalently modified with a functionalized polyethylene glycol (PEG) or other outer coating (16). QDs have a characteristically broad absorbance spectrum yet a narrow emission profile for nearly all the applicable excitation wavelengths (17), with quantum efficiencies ranging from 60-85% (18, 19).

Carbon nanotubes are allotropes of carbon with a cylindrical structure and are members of the fullerene structural family. Single wall nanotubes can have a diameter of approximately 1 nm. Carbon nanotubes have a large Stokes shift that can be excited starting around 600 nm while emitting above 900 nm (28).

Fluorescent proteins are of very common use. Green fluorescent protein, initially purified from *Aequorea victoria*, is now commonly cloned into many cells and animals. A multitude of derivatives have been developed for almost every excitation and emission wavelength. These proteins can have a large quantum efficiency, but, in general, do not have a large Stokes shift.

Diamond nanocrystals, or nanodiamonds, are produced from diamond materials that have a high nitrogen content. These nitrogen-rich diamonds are irradiated with high energy electrons which create negatively charged nitrogen-vacancy centers. The irradiated diamonds are then annealed at high temperatures to enhance the centers. These materials can have a nominal size of 100 nm, with an absorption centered at 560 nm, and emit efficiently at 700 nm. They are reported to have a quantum efficiency approaching 1, are chemically and biologically inert, and surface chemistries can be performed on them (29, 30).

Metalloporphyrins, in particular platinum-, palladium-, and ruthenium-porphyrin have several interesting properties. They are commonly excitable at 400 nm or less, while emitting at wavelengths greater than 650 nm. Many metalloporphyrins have a secondary excitation range between 500-550 nm. The metalloporphyrins listed above are also oxygen sensitive such that their luminescence intensity and lifetime decay rates are a function of the local oxygen concentration (31-33).

In the present patent application the terms "energy of a photon" and "wavelength of a light signal", are used to describe various aspects of the photon/signal emitted by the FPP-L and FPP-U. As electromagnetic radiation is considered to be both a particle (photon) and an electromagnetic wave, the same photon/wave will therefore have an energy value as well as a wavelength. The relationship between these different values is direct and generally speaking the lower the energy of a photon the greater the wavelength. Therefore when it is stated that the second photon produced by the FPP-U is of lower energy than the first photon produced by the FPP-L, it is also true/could alternatively be stated that the wavelength of the second photon is greater than the wavelength of the first photon.

In accordance with the present patent application the biological marker may be the FPP-L of the FPP used to red shift the optical signal using FUEL. Alternatively the biological marker may be the first in a series of FPPs which ultimately via series of intermediary excitations lead to the red shift of the optical signal.

References to the biological marker may therefore be a reference to the FPP-L or to the first in a series of FPPs. Alternatively the biological marker may be the FPP-U wherein it is excited by a FPP-L present in the system being studied or alternatively it may be one FPP in a cascade of FPPs.

In accordance with the present invention the term "in vitro" refers to any mixture or solution of cells, tissues, organisms or other materials derived from a living or deceased organism, in combination with chemicals, reagents under predefined conditions.

In accordance with the present invention the term "in vivo" refers to any operation performed using any mixture or solution of cells, tissues, organisms or other materials derived from a living or deceased organism, in combination with chemicals, reagents under predefined conditions when performed upon an intact animal.

In accordance with the present invention the conditions suitable for allowing the biological marker to produce at least one photon will vary depending upon the biological marker selected. For instance in the case of a bioluminescent biological marker such as luciferase it is necessary to induce/allow the expression of this enzyme and then provide conditions such that the enzyme can produce a light signal either in vivo, in vitro or in situ providing if necessary, all the component reagents which the luciferase may need to use. Likewise for a chemiluminescent biological marker it is necessary that all component reagents necessary for the reaction are present or in the case of a fluorescent biological marker it is necessary that a suitable excitation light source is present.

In accordance with the present invention the biological marker may be within the interior of the target cell, tissue or organism; or disposed upon some or all of the surfaces thereof; or both within and upon the surface of these targets.

In accordance with the present invention the FPP-U is in proximity to the target cell, tissue or organism and may in particular be located within these structures and/or upon their surface and/or are within the medium surrounding these structures, in conditions such that RET does not occur. In particular the FPP-U must be close enough to the biological marker such that the photons produced by the biological marker can excite the FPP-U, which in turn can produce at least one second photon.

In accordance with the present invention the biological marker and FPP-U are not covalently, or by any other means, bound to each other, meaning that they are not associated with each other in the target cell, tissue or organism in a manner where RET may occur.

In accordance with the present patent application a biological marker may be any bioluminescent, fluorescent or chemiluminescent molecule, compound, enzyme or other structure which produces photons of a defined nature. For instance a bioluminescent *Escherichia coli* (denoted RT57) (20) which carries a plasmid expressing the luxCDABE operon which comprises genes encoding bioluminescent products with an emission centered at 480 nm were used in some of the examples detailed herein to excite quantum dots in both in vitro and in vivo conditions.

As indicated above the inventors have now shown that BRET is not a necessary step in the red shifting of the output of a biological marker. For example, in Table 1 herein using the Cy5.5 filter, it was observed that while a significant emission from the FPP-U, QD705, was observed when the bioluminescent bacteria, RT57 and QD705 were allowed to settle together, a substantial increase was still found when nearly 3 cm in total distance, including 10 mm of Agar, separated the two components (6.10±1.79 vs. 2.21±1.00) resulting in FUEL. FIG. 4 shows the FUEL phenomenon at a distance far beyond where resonance energy transfer may occur.

This comparison indicates that (1) bioluminescent bacteria are capable of exciting QDs from a substantial distance and (2) that intentional BRET conditions are not necessary to achieve the efficient excitation of the FPP-U. The probability of BRET occurring when the luminescent source and the fluorescent probes are not bound together is minimal at best, given the relative size of the photon emitter and the fluorophore in comparison to the overall volume in which they are contained. Thus, the fact that there are more red photons when the luminescent bacteria and QD705 are in close proximity is most likely due to the increased number of photons available to excite the FPP-U. In other words, the observed photon flux is greater the closer the FPP-U is to the biological marker and there is an increase in the probability of FPP-U excitation by the photons emitted by the biological marker.

Conversely, the greater the distance between the FPP-L and FPP-U, the lower the probability of excitation, explaining the decrease in red photons. Given the substantial distances of excitation (μm-cm, FIGS. 3-6), the excitation of the FPP-U is a radiative process and does not involve the dipole-dipole interaction necessary for RET.

The method described herein although described with particular reference to bioluminescence, could be extended to other radiative energy transfer systems such as fluorescence or chemiluminescence.

The lack of a direct contact between the biological marker and the FPP-U which is producing the detected signal, could upon initial inspection be argued to indicate that there is a lack of specificity in the FUEL method, but, as is shown in FIGS. 3-6 and in Table 1, the presence of an absorber (in this case Congo Red) demonstrates the distance dependence between the biological marker and FPP-U. Thus, FUEL is capable of identifying the presence of bioluminescent bacteria in a specific location or, potentially, the interaction between a bacterium and a "labeled" cell. Also from FIGS. 3, 4, 7, one could infer that the detection of these bacteria could occur at a lower titer due to the red-shift in the photons of the FPP-U, increasing the overall sensitivity of the bioluminescence image.

In the present patent application the inventors also present a set of in vivo experiments, which were performed to determine the feasibility of FUEL under typical experimental conditions. As is seen from FIGS. 9 and 10 and Tables 3 and 4, strong evidence exists stating that the phenomenon of FUEL can be readily utilized. However, the effectiveness and usefulness of FUEL for bioluminescence imaging is largely dependent upon the FPP-U.

The inventors consider QDs to be suitable for short term use as the FPP-U in accordance with the FUEL technology described herein and there are many reasons to utilize QDs for bioluminescence imaging including broad absorption spectrum, narrow emission spectrum, significant Stokes shift and a quantum efficiency approaching 1. The QDs must be present in the host or at the target at the time of the measurement (s). In the case of FIG. 9, the mice were imaged immediately after injection (controls have shown that there was no significant diffusion over several hours that could alter the quantification of bacteria, quantum dots or their FUEL interaction).

Therefore the inventors have demonstrated that it is not necessary to use BRET in order to red-shift bioluminescent photons to the more optically desirable deep red or NIR. An unbound excitation from luminescence can and does occur between a biological marker such as bioluminescent bacteria and an FPP-U namely a QD, with this transfer occurring at substantial distances if no bioluminescent absorber is present.

The inventors have shown that the use of FUEL can substantially increase the number of red photons in both in vitro and in vivo applications thus increasing the sensitivity of the bioluminescent imaging.

In accordance with further aspects of the present invention therefore the biological marker is bioluminescent.

A multitude of bioluminescent molecules are now routinely used to label, isolate and monitor the various components of cells, viruses and related materials. Examples include aequorin or enzymes which produce photons as a product of the reaction they catalyse such as luciferases from various organisms. All such bioluminescent markers and variants can be used as the FPP-L according to the present patent application.

Alternatively the biological marker is chemiluminescent.

Alternatively the biological marker is fluorescent.

In particular the biological marker emits photons with a wavelength of less than 650 nm.

Most particularly the biological marker emits photons with a wavelength of 400-650 nm In particular the FPP-U emits photons with a wavelength longer than the wavelength of the photons emitted by the FPP-L.

In particular the FPP-U emits photons with a wavelength of 650-900 nm.

Although specific emission ranges are provided for the FPP-L and FPP-U, these components are not necessarily limited by wavelength ranges, the key technical feature is that each FPP-L has a shorter wavelength than its FPP-U, that the emission spectrum of the FPP-L overlaps with the excitation/absorption spectrum of the FPP-U and that overall the photon emitted by the biological marker (whether the FPP-L or FPP-U) is more easily detected.

According to a further aspect of the present invention the biological marker and/or FPP-U may be present as single or multiple copies within the cell, tissue or organism being worked upon.

According to a further aspect of the present invention the method comprises determining the presence of at least two photon producing biological markers in a cell, tissue or organism; wherein each of the at least two biological markers emits photons in a non-overlapping range of wavelengths which excite at least one of two subset of said FPP-U which emits at least one photon, wherein the at least one photon emitted by each subset FPP-U are in a non-overlapping range of wavelengths.

As well as using FUEL to transduce the signal from a single type of biological marker, it would also be possible to transduce several non-overlapping signals from several biological markers by providing different subsets of FPP-Us. Further each of these subtypes of FPP-U emits non-overlapping signals so allowing the different biological signals to be visualized.

In accordance with this particular aspect of the present invention, the different subsets of FPP-Us may be the same type of molecule or alternatively they may be different types of molecules. In a preferred embodiment one subset of the FPP-U is a QD and the other subset is a carbon nanotube.

In particular the FPP-Us comprise means to target it to specific portions of said cell, tissue or organism.

A variety of means are available to target a particular molecule or compound to an intra- or extracellular location, including nuclear localization signals, cell penetrating peptides, antibodies and aptamers. The combination of such a component with the FPP-U would therefore allow the FPP-U to be positioned in a optimal location so as to receive (if present) the photons from the biological marker and transform this into a detectable signal.

In particular the biological marker may be free or associated with a component of the target cell, tissue or organism. For instance, the biological marker may be part of a fusion protein In particular the FPP-U is disposed inside the cell, tissue or organism.

Alternatively the FPP-U is disposed outside of the cell, tissue or organism.

Alternatively the FPP-U is disposed inside and outside of the cell, tissue or organism.

Using the specific mechanisms listed above to position a FPP-U inside or outside of a cell, tissue or organism of interest, or simple by timing the visualization step so as to allow the FPP-U to diffuse fully to the target, the present method allows as appropriate the positioning of the FPP-U so as to best elucidate the signal produced by the biological marker.

According to a further aspect of the present invention the biological marker (FPP-L) and its pair (FPP-U) may be associated with each other, such as components of a larger molecule, but the FPP-L and FPP-U are not associated with each other so as to allow RET to occur.

According to a second aspect of the present invention there is provided a kit for performing the method according to the present invention, comprising at least:

at least one FPP-U according to the present invention; and
instructions for the performance of the method according to the present invention wherein the at least one FPP-U has an excitation spectrum which overlaps with the emission spectrum of a biological marker and so when disposed in proximity to the biological marker in a system being studied, will emit photons via the FUEL mechanism which in turn can be detected.

In particular according to this aspect of the present invention the kit may comprise at least one biological marker according to the present invention.

In particular the kit further comprises a compound which absorbs the photons produced by said biological marker.

By providing an absorber of the photons produced by the biological marker, the user of the kit whilst performing the method can control the distance between the biological marker and FPP-U which will allow the FPP-U to be excited, given the presence of the absorber will reduce this distance as a function of its concentration. A multitude of possible absorbers are known for every conceivable emission wavelength of the biological marker and all such absorbers are encompassed by the present patent application.

In accordance with a further aspect of the present invention there is provided a kit for performing the method according to the present invention, comprising:

at least one FPP-L according to the present invention; and instructions for the performance of the method according to the present invention Wherein the at least one FPP-L has an emission spectrum which overlaps with the excitation spectrum of a biological marker and so when disposed in proximity to the biological marker in a system being studied will cause the biological marker to emit photons via the FUEL mechanism which in turn can be detected.

In accordance with a further aspect of the present invention there is provided a kit comprising a plurality of FPPs with sequentially overlapping emission and excitation spectra which can be used in a cascade FPP system as detailed herein.

According to a third aspect of the present invention there is provided the use of FPP-U, for example unbound QDs, to determine the presence of a photon producing biological marker in a cell, tissue or organism of interest wherein FUEL occurs between the biological marker and unbound QDs, leading to a red shifting of the signal emitted by the biological marker.

In accordance with a further aspect of the present invention there is provided the use of FPP-L, to produce a photon and determine the presence of a biological marker in a cell, tissue or organism of interest wherein FUEL occurs between the FPP-L and the biological marker, leading to a red shifting of the signal.

BRIEF DESCRIPTION OF THE DRAWINGS

For a better understanding of the invention and to show how the same may be carried into effect, there will now be shown by way of example only, specific embodiments, methods and processes according to the present invention with reference to the accompanying drawings in which.

DETAILED DESCRIPTION

Figure 1:
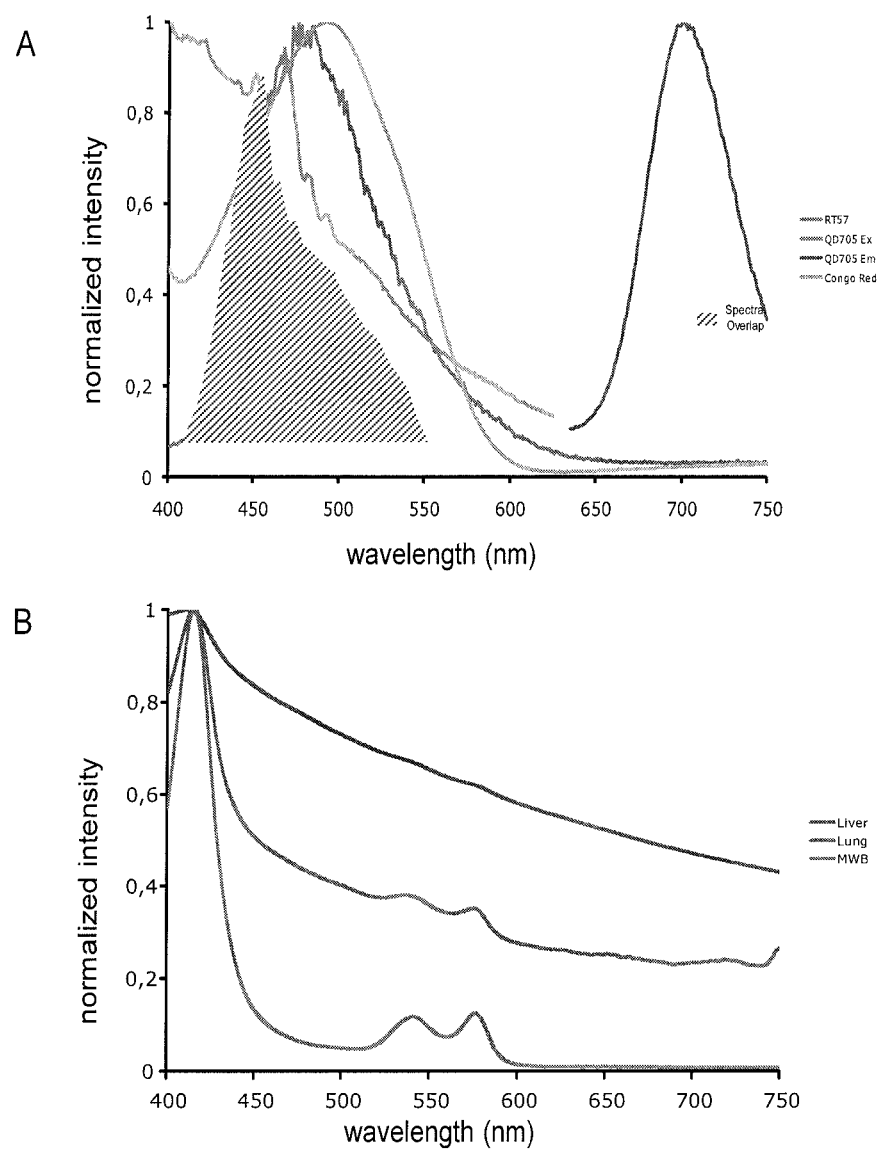
FIG. 1: Absorption and Emission Spectra of Different Elements of the Experiment.
A. Emission spectrum of RT57, excitation and emission spectrum of QD705, and the absorption spectrum of Congo Red. The hashed (///) region indicates the spectral overlap between the RT57 emission and the QD705 excitation.
B. Absorption spectra of mouse lung, blood, and liver.

There will now be described by way of example a specific mode implemented by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

Example 1

Materials and Methods

Common Reagents

The bioluminescent *E. coli* carrying the plasmid expressing the lux operon (pUC18-mini-Tn7T-Gm-lux referred to as RT57) is described in Choi et al. (20) and is noted as RT57 throughout. Qtracker 705 non-targeted quantum dots were acquired from Invitrogen and kept in the dark at 4° C. until use (noted as QD705). To prepare the Agar plates, 25 mL of warm sterile agar was added to a 10 cm Petri dish under sterile conditions and allowed to cool. Congo Red (Sigma) was prepared as a 1% w/v in sterile $H_2O$. Low melting agarose (Lonza, France) was used for pearl construction. Normal physiological saline (0.9% NaCl, referred to as PS) was prepared in house and used for all dilutions. For the Congo Red+Agar plates (CRAgar), 4 mL of 1% w/v Congo Red (Sigma) in sterile $H_2O$ was added to 400 mL of warm sterile agar for a final dye concentration of 0.01% in Agar. The solution was well mixed and then 25 mL were added to a 10 cm Petri dish and allowed to cool. The resulting dishes contain a 5 mm thick layer of Agar or CRAgar. After the Agar and CRAgar had solidified, the prepared plates were inverted and stored at 4° C. until used. For all animal experiments, female six-week old Balb/c mice (Janvier, France) were used.

Bacteria Preparation

The day before imaging, an overnight culture of the RT57 was established. The following morning, the $OD_{600}$ was acquired and when necessary, plated depending on the appropriate dilution performed to achieve a final concentration of 1000 bacteria/5 μA of saline. The bacteria were then plated depending on the desired orientation (generally a 3×4 matrix of 5 μL aliquots).

Long Distance Excitation of QD705

Black tape was used to create two 2 mm×3 mm optical windows on a reduced-volume disposable cuvette (Ratiolab, Germany), with the two windows situated on opposite faces of the cuvette, and located near, but away from, the base. This modified cuvette was filled with 1 mL of RT57 stock from an overnight culture, covered by a piece of black paper, and placed into the Ivis imaging system. The black paper inhibited the observation of the RT57 bioluminescence. Two unmodified reduced volume cuvettes were filled with either 1 mL of PS, or 1 mL of the previously described QD705 solution, were then placed on either side of the modified cuvette containing RT57 such that the three cuvettes were axially aligned and at a distance of 10 mm between the central and exterior cuvettes (face to face). The resulting luminescence was observed for the Open and QD705 filter sets. After acquisition, the distance between the two unmodified cuvettes and the central cuvette was increased by 5 mm, and the luminescence observed. This was repeated up to a total separation of 30 mm for three different bacterial cultures.

In an alternative experiment a 5 μl aliquot of stock RT57 was placed onto the center of an empty Petri dish. Starting at a distance of 5 mm (center to center) from the bacteria, 2 μl aliquots of QD705 were placed radiating outward, increasing in 5 mm intervals up to a total distance of 2 cm. The plate was imaged for 300 s using the QD705-specific filter set. A fluorescence image was acquired to verify QD705 location.

Increase in Red Photon Generation from the Addition of QD705.

Figure 7:
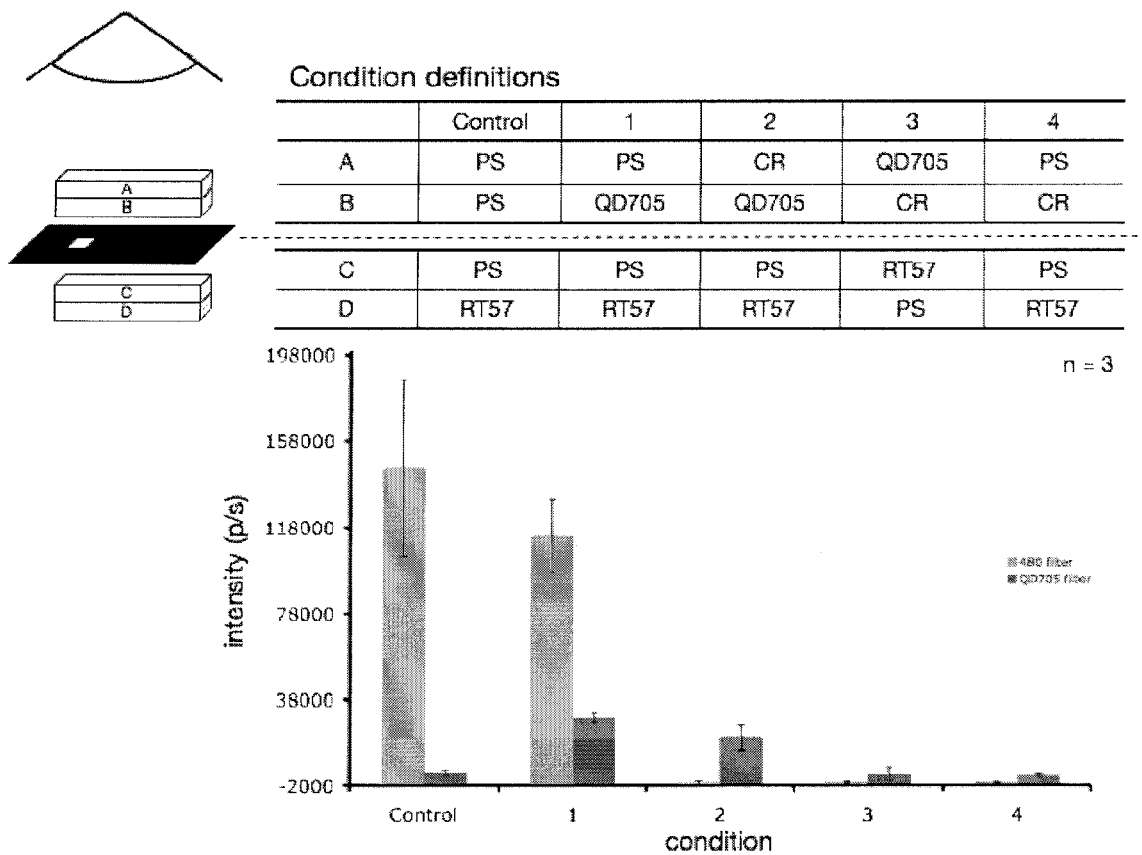
FIG. 7: Increase in red photon generation from the addition of QD705 was ascertained using several experimental conditions were established using two quartz tandem cuvettes separated by a piece of black paper. A small window was cut into the paper in order to allow the bioluminescent photons to pass.

Multiple experimental conditions were established using two quartz tandem cuvettes (inset table FIG. 7, PS: physiological saline; QD705: QD705 solution; RT57: bioluminescent *E. coli*; CR: Congo Red) separated by a piece of black paper. A small window was cut into the paper in order to allow the bioluminescent photons to pass. The paper also provided a physical separation between the two cuvettes ensuring that no physical contact could occur between the QD705 and the RT57. For each condition the luminescence intensity was observed under both the RT57- and the QD705-specific filter sets (noted as 480 and QD705 respectively), with each condition performed in triplicate.

Spectral Acquisition

A Perkin-Elmer UV/Vis dual path spectrometer with a 1 nm slit width and set to a scan rate of 480 nm/min was used to acquire the absorption spectra for the Congo Red, whole mouse blood, liver, and lung (FIG. 1). Sterile water was used as the reference. For each acquisition, 1 mL of each analyte was added to a 1 mL plastic cuvette with a 1 cm path length. The RT57 bioluminescence emission spectrum was recorded with a PTI Quanta-Master QM4CW spectrofluorometer (PTI, Lawrenceville, N.J.) using a 1 cm path length quartz cuvette thermostated at 25° C. Luminescence was recorded from 400 to 750 nm with 5 nm slit widths. The QD705 excitation and emission spectra were acquired with 5 nm slit widths.

In Vitro Bioluminescence Imaging

An IVIS 100 whole animal imaging system (Xenogen Corporation, Caliper Life Sciences, Alameda, Calif.) equipped with a cooled CCD and a filter wheel was used to acquire all bioluminescent images. The filters used were a 610 long pass (610LP) and a Cy5.5 band pass (695 nm-770 nm, also referred to as the QD705 filter). One location within the filter wheel was kept empty for total light detection, termed the Open filter set. For each experiment, the CCD was cooled to −105° C. and the dark box warmed to 37° C. Unless otherwise stated, the acquisition settings for the Living Image (Xenogen) software version 3.1 were set as the following: 5 minute acquisition time for all three filter sets, 8× bin, field of view C (20 cm), and f-stop 1. In the case of a time course experiment, an image sequence was established such that the Open, 610LP, and Cy5.5 images were acquired sequentially and then followed by a 45 minute delay creating a one hour image cycle. This cycle was allowed to repeat until desired.

Distance Excitation of Quantum Dots Using Unbound Bioluminescent Bacteria

Figure 3:
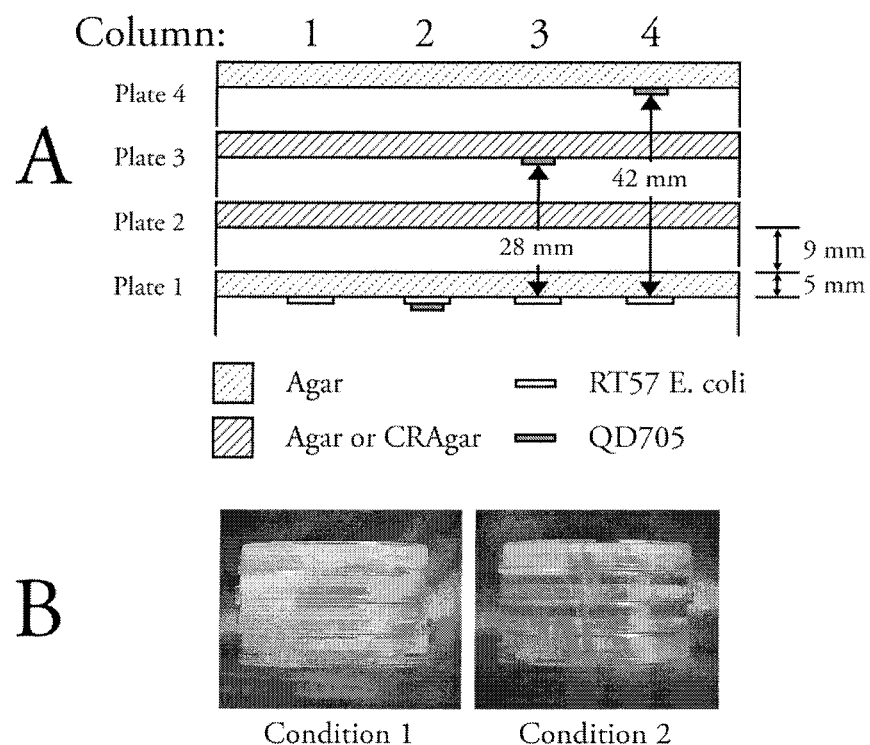
FIG. 3: Experimental Setup for the FUEL Distance Dependence Determination.
A. Schematic diagram showing the positioning of plates and the localization of RT57 and the QD705. The distances between the bacteria and QD705 are indicated.
B. Photograph of the plate setups of Condition 1 (four Agar plates) and Condition 2 (two Agar plates and two CRAgar plates).

Two different conditions were established to measure the effect of distance on the RT57-QD705 photon production, with Condition 1 involving four Agar plates and Condition 2 using two Agar plates and two CRAgar plates (FIG. 3). Before the placement of the bacteria and QD705, the required plates were removed from the 4° C. storage, allowed to warm to room temperature, and checked for contamination. For Condition 1, twelve 5 μL aliquots of the bacterial solution were pipetted in a 3 row by 4 column (3×4) matrix onto an Agar plate with gentamycine at a final concentration of 50 μg/mL. The droplets of bacteria, containing 1000 cells each, were allowed to settle into the Agar (Plate 1). A second Agar plate was set aside until the final construction of the plate stack (Plate 2). Three aliquots of 2 μL of QD705 were then pipetted onto the third Agar plate (Plate 3) such that, when stacked on top of the plate containing the bacteria (Plate 1), each aliquot of QD705 would be vertically aligned with each aliquot of bacteria for column 3. A second set of QD705 aliquots were placed onto the fourth Agar plate (Plate 4) with each aliquot aligned with the corresponding bacteria of column 4 on Plate 1. Finally, after ensuring that the bacteria had settled into the Agar, a 2 μL aliquot of QD705 was added directly onto each bacterial aliquot located in column 2 on Plate 1. The plates were inverted and stacked in order with Plate 1 on bottom, then the empty Plate 2, followed by Plates 3 and 4. The stack was then placed into the Ivis 100 and the image sequence started. For Condition 2, the same procedure was followed except Plates 2 and 3 consisted of CRAgar instead of Agar. The total plate height was measured to be 14 mm with an Agar or CRAgar depth of 5 mm (FIG. 3). The total distance between the RT57 and the corresponding QD705 aliquot were as follows: 0 mm for Column 2, 28 mm for Column 3, and 42 mm for Column 4.

Unbound Excitation of QD705

To determine if the bioluminescent RT57 were able to excite the QD705 without the need of physical binding, a series of 1.5 mL Eppendorf tubes were prepared. The first tube included 10 μL at of bacterial stock diluted up to 100 μL using physiological saline (PS). A second tube was prepared using 10 μL of bacterial stock, 4 μL of QD705, and 86 μL, of PS. Two luminescent controls were established with the first including 4 μl of QD705 diluted up to 100 μL and the second consisting of 100 μL PS only. All four tubes were gently mixed by pipette to create homogenous solutions and placed into the imaging system with black plastic separators placed between each tube to minimize signal crossover. The resulting bioluminescence was observed for 5 s under both filter sets. Presence of QD705 was confirmed using fluorescence imaging.

Ex Vivo Bioluminescent Imaging

Three female six-week old Balb/c mouse were anaesthetized with Ketamine/Xylazine. For each mouse a cardiac puncture was performed to obtain around 1 mL of blood. The liver was removed and placed into 2 mL of chilled PBS. Finally, the lungs were also removed and placed into 1 mL of chilled PBS. The organs were then homogenized using a mechanical homogenizer and, along with the blood, were kept on ice until further use. Each mouse was sacrificed by neck dislocation. The organs were then homogenized using a mechanical homogenizer and along with the blood, were kept on ice until further use. All animal experiments were done in accordance to French National Ethics regulations.

Prior to the mouse preparation, a glass bottom black 96 well plate was altered so that the base of the plate could rest evenly onto a 10 cm Petri dish. A piece of black paper that had twelve 1.5 mm diameter holes in a 3×4 orientation was placed in between the 96 well plate and an agar plate such that the pinholes were properly aligned with the wells of the 96 well plate. 5 μL aliquots of bacteria stock were then pipetted onto the agar directly aligned with the pinholes and the wells. After having time to settle, 2 μL aliquots of QD705 were placed onto the second and fourth columns of bacteria. The setup was then placed into the Ivis 100 at 37° C. and bioluminescence confirmed. Then, 50 μL aliquots of blood, homogenized liver, or homogenized lung from each mouse were appropriately distributed and the previously described image sequence acquired.

In Vivo Bioluminescent Imaging

Female Balb/c mice were anaesthetized with isoflurane (2.5%). Under anaesthetic, mice were injected intramuscularly in the left thigh to a depth of 3 mm with 25-50 μL of bacterial suspension with or without QDs and imaged using the IVIS 100. A brightfield image was taken first and followed by bioluminescent images with the Open, 610LP, and Cy5.5 filters. Images were analyzed using the Living Image (v 3.1, Xenogen corp.) software.

FUEL Imaging In Vivo Using "Pearls"

To demonstrate FUEL in vivo, 2% agarose pearls consisting of an RT57-based core layered by agarose or a mixture of agarose and QD705 were constructed. Briefly, to create an individual "pearl", 12.5 μL of RT57 stock was mixed with 12.5 μL warm 4% agarose and pipetted onto parafilm. After the 25 μL pearl core was allowed to cool, a mixture of either 5 μL of PS or 5 μL QD705 stock and 7.5 μL of 5% agarose was pipetted onto the pearl core, forming the Control and FUEL pearls, respectively. After construction of the pearls, three female six-week old Balb/c mice were chemically anesthetized using Ketamine/Xylazine. The hind limbs, both the dorsal and ventral sides, of all three mice were then shaved using an electric razor. A small incision was placed on the interior of both hind limbs, allowing for the subcutaneous placement of either the control (RT57) or FUEL (RT57 and QD705) pearl. The mice were then placed into the Ivis 100 and the luminescence observed from the ventral side for both the Open and QD705 filter sets. The mice were then rotated and the luminescence observed from the dorsal side for both filter sets.

Example 2

Results

Spectral Comparison

A normalized UV/Vis absorbance plot of Congo Red (CR) overlaid with the bioluminescence emission spectrum of the RT57 and the excitation/emission spectrum of the QD705 can be seen in FIG. 1A. As is shown, the excitation spectrum of the QD705 greatly overlaps the bioluminescent emission, while the fluorescence emission of the QD705 was found to be centered at 703 nm. In order to acquire a useful absorbance spectrum, the blood was diluted 300 times in sterile $H_2O$, while the liver and the lung were diluted 200 times each, also in sterile $H_2O$ (FIG. 1B).

As can be seen from FIGS. 1A and 1B, the emission of the QD705 is located in a region of minimal absorption and scatter by the blood, liver, and lung while the bioluminescent emission of the RT57 is greatly perturbed by the scattering/absorbing agents. The locations of these emission maxima greatly illustrate the benefit of red-shifting the emitted photons.

Unbound Excitation of QD705 by Bioluminescent Bacteria in Suspension

To determine if bioluminescent *E. coli* could excite QD705 without the need of any coupling chemistry or binding, solutions of RT57 and QD705 were distributed alone or mixed in separate tubes and the resulting luminescence production compared to three controls (RT57 alone, QD705 alone, and PS) under two different emission filter sets (Open and Cy5.5).

Figure 2:
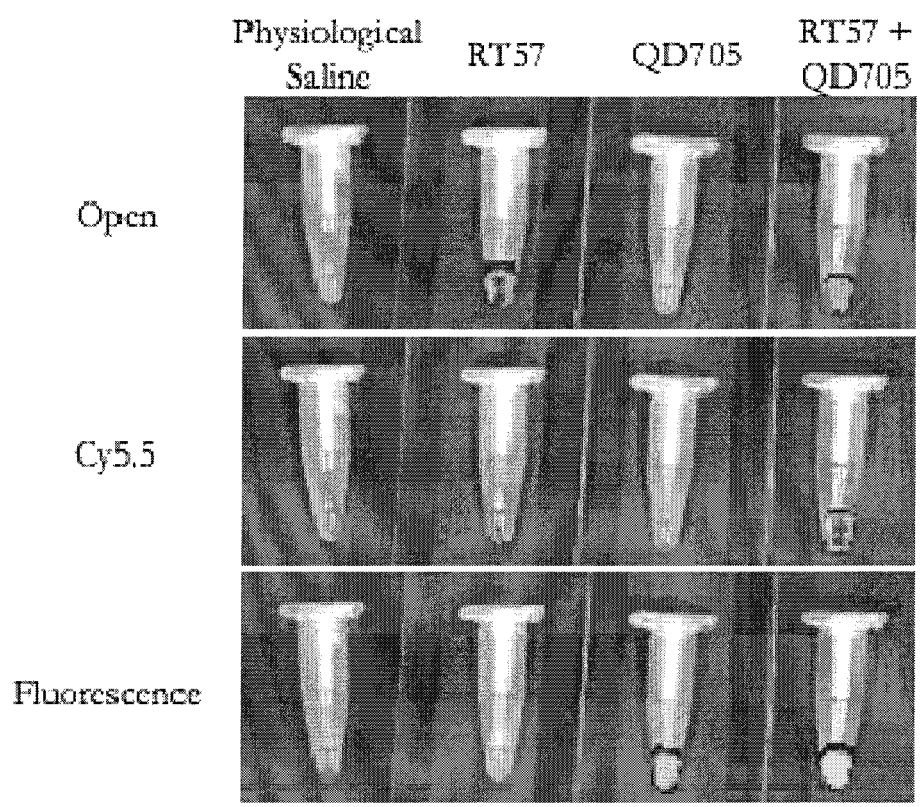
FIG. 2. Unbound excitation of QD705 using bioluminescent *E. coli*. Physiological water (Column 1), RT57 (Column 2), QD705 (Column 3), and a mixture of RT57 and QD705 (Column 4) were aliquoted into separate 1.5 ml eppendorf tubes and the resulting luminescence observed under Open and Cy5.5 filter sets (Rows 1 and 2, respectively) with the exposure time set to 5 s. Under the Open filter set, similar levels of luminescence were observed for both the RT57 and RT57+QD705, while no luminescence was observed for the two controls. A substantial increase in the number of photons was observed for the RT57+QD705 mixture as compared to the RT57 alone when observed under the Cy5.5 filter set. The presence of the QD705 was confirmed by fluorescence excitation using a 0.25 s exposure time (Row 3).

As can be seen from FIG. 2, both the RT57 and the RT57+QD705 emit photons in the presence of the Open filter. As expected, no luminescence was observed from bioluminescent controls (QD705 or PS alone; columns 1 and 3, rows 1 and 2). In the presence of RT57 we observed comparable robust bioluminescent signal in the absence of emission filters (columns 2 and 4, row 1), with bacteria alone (column 2, row 1) and with RT57+QD705 (column 4, row 1).

However, by stark contrast when observed through the Cy5.5 emission filter, we observed some ten-fold more signal from RT57+QD705 (column 4, row 2) compared with luminescent bacteria alone (column 2, row 2), suggesting that the presence of QD705 had caused a shift in the wavelength of the emitted light, such that part of it now passed through a deep red emission filter. No luminescence was observed from the controls. This strongly suggests that bioluminescent bacteria alone are able to excite QD705. A normalized bioluminescence emission spectrum of the RT57 and the excitation/emission spectrum of the QD705 are shown (FIG. 1). The excitation spectrum of the QD705 overlaps with the peak emission of RT57 bioluminescence while the fluorescence emission of the QD705 was centered, as expected, at 705 nm. In view of the spectral overlap and the results presented here, RT57 bioluminescence alone is sufficient to excite QD705.

Distance Dependence of the Bacterial Luciferase—QD705 FUEL Probe Pair

Figure 4:
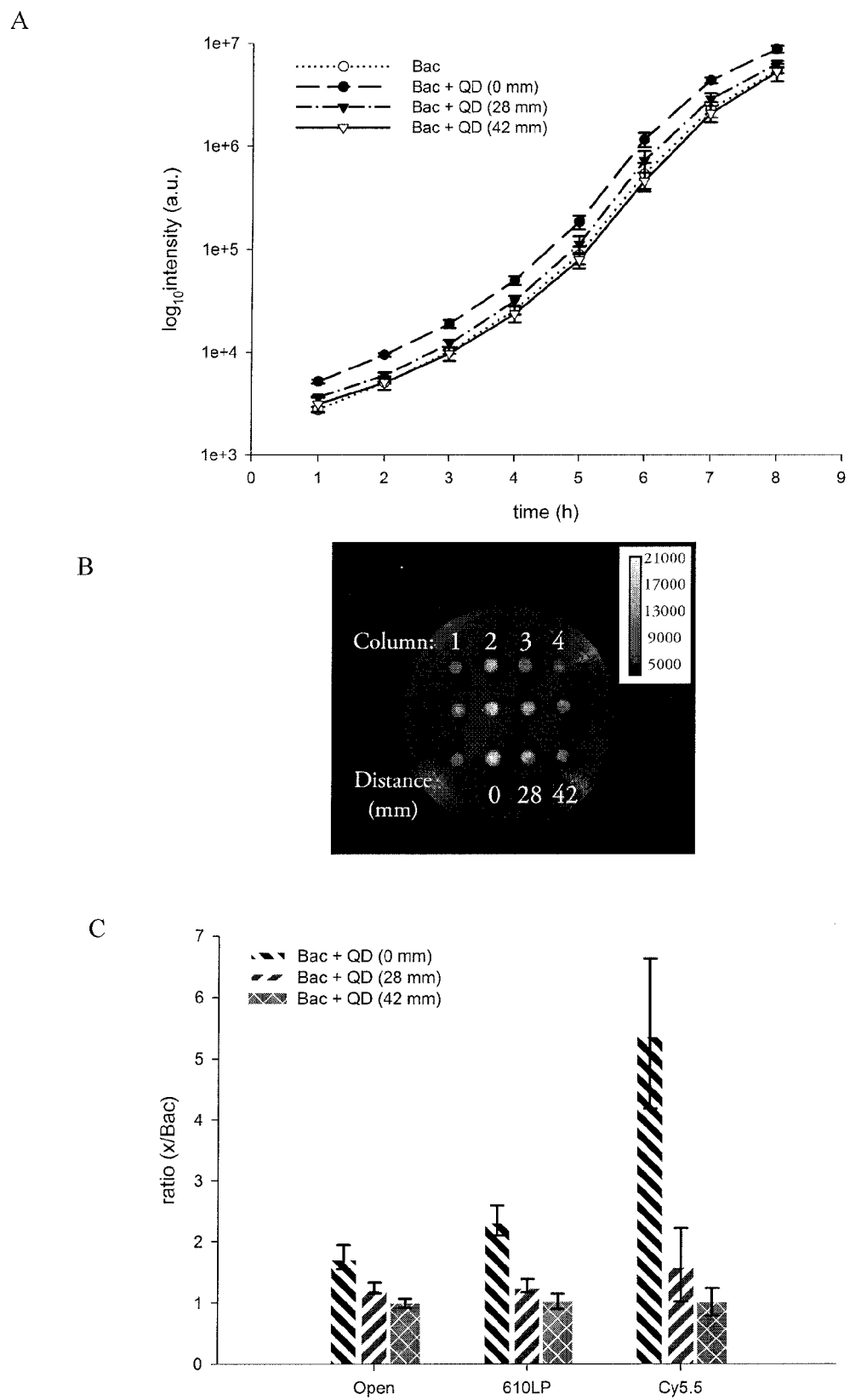
FIG. 4: Overnight Growth Experiment for Condition 2.
A. Overnight growth curve of bioluminescent bacteria under Condition 2.
B. Example of the last time point image for Condition 2.
C. Comparison of Columns 2, 3, and 4 to Column 1 showing the enhancement of the detectable photons.

A simple model mimicking the optical absorption of mouse blood, liver, and lungs was developed in order to demonstrate the importance of red shifting of the bioluminescent photons via trivial excitation. The common pigment Congo Red (CR) was found to have an absorption spectrum that, similar to the mouse blood, liver, and lungs, overlapped with the RT57. The CR also displayed very little absorbance at 705 nm. The effect of the absorber, CRAgar, on the detectable photons was observed by stacking plates of Agar and CRAgar above aliquots of the RT57 and RT57+QD705 under two different conditions (FIG. 3). As described previously, three consecutive 5 minute acquisitions were acquired using a different filter set for two different conditions. Condition 1 included the use of four standard agar plates while Condition 2 replaced the central two agar plates with CRAgar plates (FIGS. 3A and 3B). Growth experiments were repeated in triplicate for each condition, and were observed using the Ivis 100. FIG. 4A shows the increase in total photon flux for Condition 2 over time while FIG. 4B shows a typical bioluminescent image acquired at the end of a growth experiment for Condition 2. As can be seen, column 2 (RT57+QD705) is significantly brighter than the other columns. This difference can be more clearly observed in FIG. 4C. Here, the total photon flux for columns 2, 3, and 4 were normalized to column 1 (RT57 only). A significant increase in the total photon flux is observed for column 2, a small increase for column 3, and essentially no increase in column 4.

As is seen in Table 1, there is an increase in the photon flux for column 2 in both Conditions under the Open filter set. A similar increase is also observed for column 3 in Condition 1, while a smaller increase is observed for Condition 2. This can be explained due to the presence of the CRAgar plates within Condition 2. The CRAgar plate situated between Plate 1 and Plate 3 decreases the number of RT57 photons available to excite the QD705 that lie on Plate 3. This is important because this effect suggests that the QD705 must be optically available to the RT57 in order to have the shift in photons occur. Further evidence of this is also seen when column 4 is compared to column 1 for Condition 2. Here, the ratio between the columns is centered around 1, indicating that there is no enhancement when two plates of CRAgar are present. Yet, for condition 1, a slight enhancement is observed even with two plates of Agar between the RT57 and the QD705 (Column 4). Thus, without the absorber, there is no specificity to the excitation of the QD705. The bacteria can be a substantial distance away. This is not desired when observing the bacterial evolution within an animal. Under each Condition and for each filter set, the maximum enhancement is observed for Column 2 (RT57+QD705). The increased enhancement observed for both the 610LP and Cy5.5 filter sets verifies the red-shift of the bioluminescent photons due to the presence of QD705.

TABLE 1

Distance dependence of QD705 excitation with bioluminescent RT57.*

|  | Column | Distance (mm) | Open | 610LP | Cy5.5 |
| --- | --- | --- | --- | --- | --- |
| Agar | 2 | 0 | 1.43 ± 0.43 | 2.57 ± 0.68 | 6.10 ± 1.79 |
|  | 3 | 28 | 1.46 ± 0.60 | 1.97 ± 0.88 | 2.21 ± 1.00 |
|  | 4 | 42 | 1.09 ± 0.27 | 1.17 ± 0.30 | 1.13 ± 0.31 |
| CRAgar | 2 | 0 | 1.75 ± 0.20 | 2.35 ± 0.24 | 5.41 ± 1.22 |
|  | 3 | 28 | 1.24 ± 0.09 | 1.28 ± 0.11 | 1.62 ± 0.60 |
|  | 4 | 42 | 0.99 ± 0.08 | 1.02 ± 0.12 | 1.01 ± 0.23 |

*Each column was normalized to column 1 of the corresponding Condition, n = 24.

However, when looking at the ratio of improvement from Table 1, one must not assume that the Cy5.5 filter set is ideal because far fewer photons are actually detected due to the band pass. This filter is much more specific for the emission of the QD705. While the 610LP allows far more photons to reach the CCD than the Cy5.5, it is still less than the Open. Thus, while the ratio of improvement is smaller, the number of photons detected is far greater. With the Open filter set one achieves an increased sensitivity, acquiring the emitted photons from the QD705 and any unabsorbed and unscattered RT57, while the use of the 610LP or the Cy5.5 allows for an increased specificity to the QD705.

Figure 5:
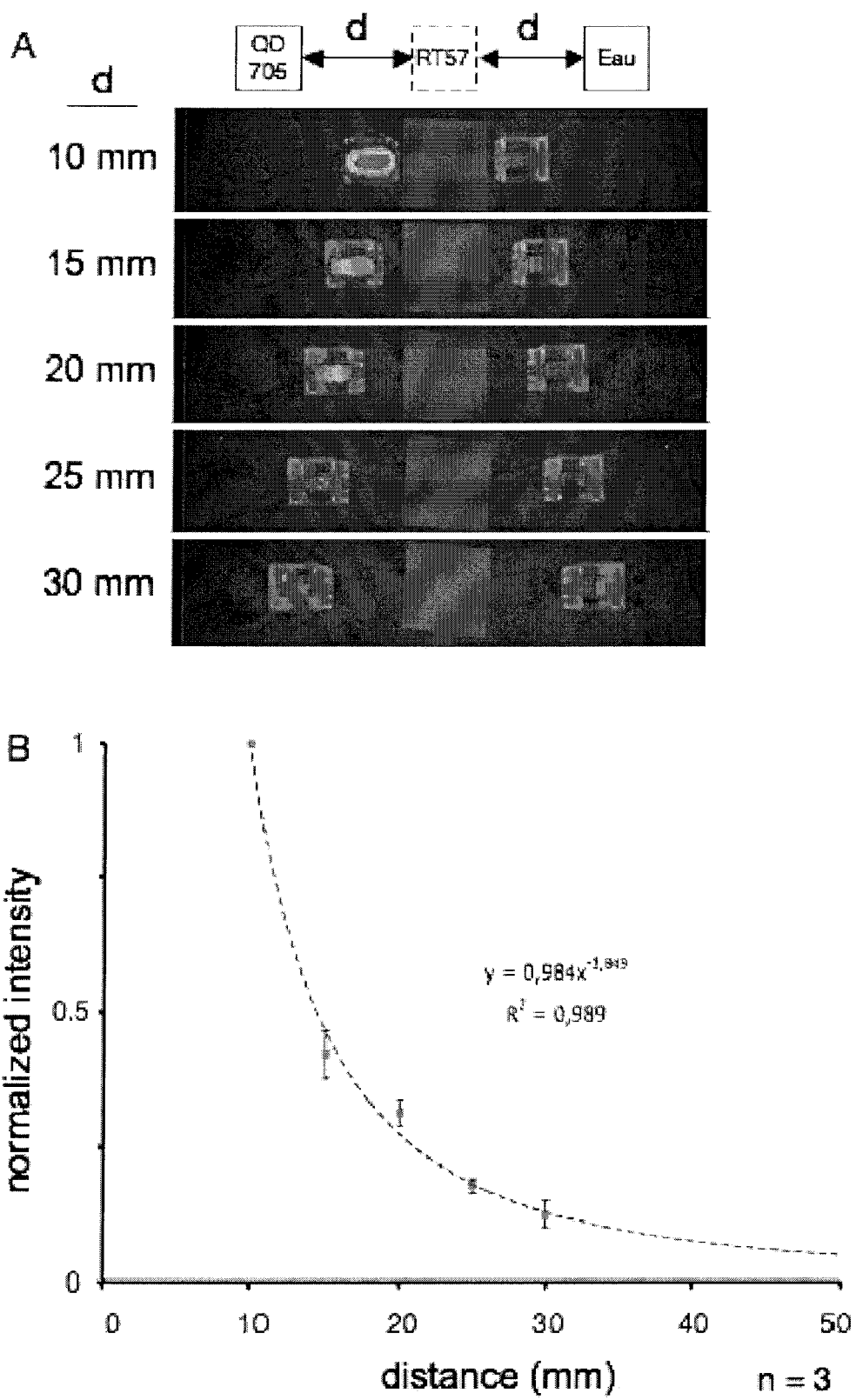
FIG. 5: The distance dependence of the FUEL effect. An aliquote of bioluminescent *E. coli* (not visible: covered by a piece of black paper) is placed between two cuvettes filled with either QD705 (left) or water (right) at increasing distances and the resulting luminescence detected. Normalized luminescent intensities from the FUEL effect as a function of distance. The distance dependence of the FUEL effect was repeated in triplicate using three different bacterial cultures.

In a further set of experiments an aliquote of bioluminescent E. coli (not visible: covered by a piece of black paper) was placed between two cuvettes filled with either QD705 (left) or water (right) at increasing distances and the resulting luminescence observed under either the Open or QD705 specific filter sets. As is observed under both filter sets, the luminescence of the QD705 decreases as a function of distance while no luminescence is observed from the water alone. The results are shown in FIG. 5A. These results illustrate that (1) in the absence of any quencher the FUEL effect can occur over substantial distances and (2) that the FUEL effect occurs by a light radiation process since there is no physical connection between the bioluminescent source and the fluorescent reporter.

Normalized luminescent intensities were calculated as a function of distance. The distance dependence of the FUEL effect was repeated in triplicate using three different bacterial cultures. The resulting luminescence for the QD705 filter set were normalized to the most intense value, which occurred at a distance of 1 cm (Top). As can be seen in FIG. 5B, the variance in the normalized intensities was quite insignificant. A polynomial curve was fitted to the luminescent intensity with significant agreement.

Increase in Red Photon Generation from the Addition of QD705.

Multiple experimental conditions were established using two quartz tandem cuvettes separated by a piece of black paper. These conditions are shown schematically in FIG. 7, where in PS: physiological saline; QD705: QD705 solution; RT57: bioluminescent E. coli; CR: Congo red.

A small window was cut into the paper in order to allow the bioluminescent photons to pass. The paper also provided a physical separation between the two cuvettes ensuring that no physical contact could occur between the QD705 and the RT57. For each condition the luminescence intensity was observed under both the RT57- and the QD705-specific filter sets (noted as 480 and QD705 respectively), with each condition performed in triplicate.

As can be seen, in the absence of QD705 (condition Control), very few red photons were observed. However, a nearly 8-fold increase in the red photon production was observed by simple addition of the QD705 to the optical path (condition 1). In the presence of an absorber, CR (condition 2), this increase remains the same, illustrating the powerful contrast enhancement due to the FUEL effect in the presence of an absorber. Further, when the absorber is placed between the bioluminescent source and the QD705 (condition 3), the total photon production is reduced dramatically and the red photon production is similar to the Control, indicating that the FUEL effect is no longer occurring. This also highlights the specificity of FUEL inasmuch as the FPP-L and FPP-U must be in close proximity in the presence of an absorber, but not necessarily in molecular proximity. By way of positive control, similar values were observed in the absence of QD705, and the presence of CR (condition 4), verifying that the loss of the FUEL effect in condition 3 was due to the blue light absorbance of CR between the bacteria and the QD.

Photon Transmission Through Ex Vivo Samples

Before injecting mice with QDs and bacteria, in triplicate from three different mice, MWB (mouse whole blood), homogenized liver and homogenized lung were used in order to simulate in vivo conditions. Here, an agar plate with RT57 and RT57+QD705 was prepared as previously described. A piece of black paper containing a pinhole was placed over an Agar plate such that the pinhole was properly aligned with the aliquots of RT57 and RT57+QD705. Finally, a black 96 well plate was placed on top of the black paper and agar plate.

Figure 8:
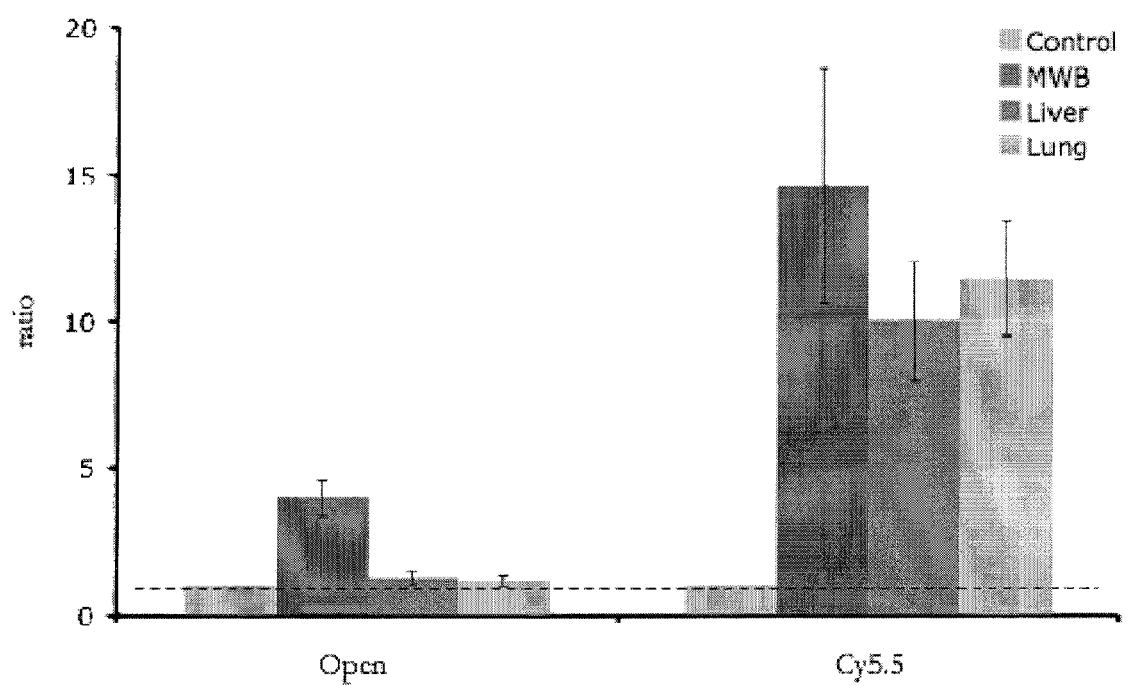
FIG. 8. Improved luminescence detection through ex vivo samples. The luminescence of three distinct RT57+QD705 mixtures was observed through MWB, homogenized liver, or homogenized lung, and normalized by the observed luminescence from the RT57 alone under the same conditions. While an increase in the number of observed photons was found for the mixture under the Open filter set (Left), a rather sizeable increase in the number of red photons was observed under the Cy5.5 filter set (Right).

As can be seen within FIG. 8 and Table 2, in the presence of MWB under the Open filter, the RT57+QD705 had an increase of nearly 4 times the total photon flux compared to the bacteria alone. However, a minimal increase in the total photon flux was observed for the liver and lungs. By contrast, the ratio was dramatically increased when using the Cy5.5 filter verifying the QD705 excitation resulting in a substantial increase in red photon production. The results of this in vitro experiment strongly suggest that the presence of the QD705 red shifts the RT57 photons away from the absorption maxima of MWB thus increasing the total number of detectable photons.

TABLE 2

Improved photon transmission in the presence of Blood and Tissue.*

|  | Blood | Liver | Lung |
|---|---|---|---|
| Open | 3.98 ± 0.58 | 1.26 ± 0.25 | 1.14 ± 0.19 |
| 610LP | 4.59 ± 0.38 | 2.61 ± 0.42 | 4.75 ± 0.64 |
| Cy5.5 | 14.62 ± 3.98 | 10.01 ± 2.06 | 11.44 ± 1.95 |

*The improved transmission through each absorber was normalized to the number of photons detected from RT57 alone, n = 3.

Evidence of In Vivo QD Excitation Using Bioluminescent Bacteria

Figure 9:
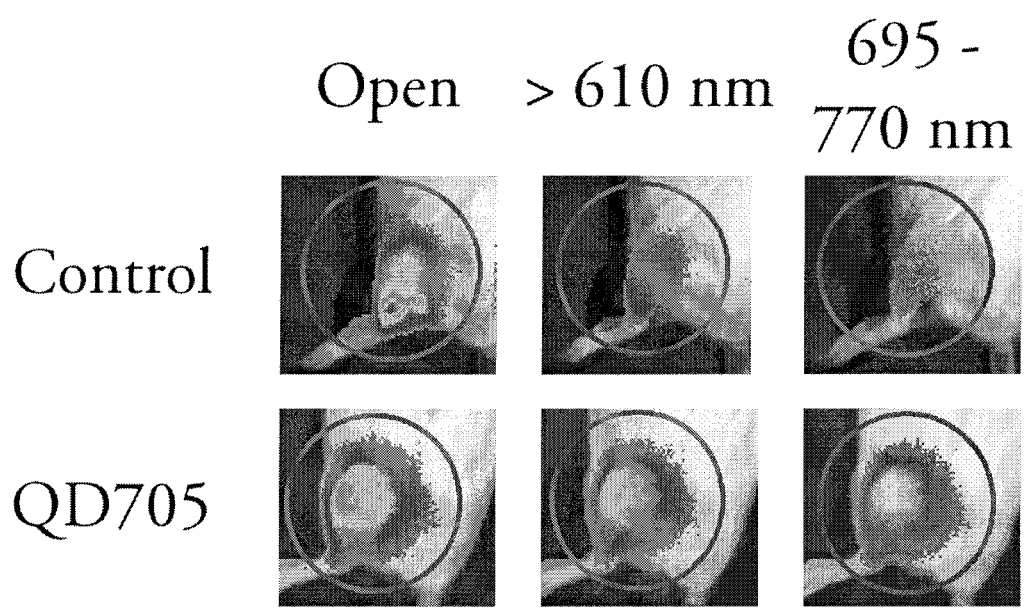
FIG. 9: in vivo Example of Detectable Photon Enhancement in the Presence of QD705. Images were acquired in Open, 610LP, and Cy5.5 filter sets after intramuscular thigh injection of bacteria and bacteria+QD705.

In order to demonstrate the capabilities of this technique, an in vivo proof of principle experiment was performed. QD705 and a bacterial suspension were sequentially injected into the thigh of a mouse under anesthetic. A second mouse was injected with bacteria alone and used as a control for the standard bioluminescence production. The bioluminescence productivity of each mouse was collected simultaneously under the three different filter sets (FIG. 9). As can be seen, an increase of the measured bioluminescence was observed for the QD705 injected mouse under each filter set. Table 3 displays the significant shift in the detected photons when the QD705 are present.

TABLE 3

Demonstration of in vivo QD705 excitation.

|  | 610LP/Open | Cy5.5/Open |
|---|---|---|
| Control | 0.247 | 0.077 |
| QD705 | 0.690 | 0.604 |

As can be seen from Table 3, only 25% of the detected bioluminescent photons are longer than 610 nm for the bioluminescent bacteria alone. Even more notable is that less than 10% of the bioluminescent photons occur within the Cy5.5 filter set. There is a dramatic difference when the QD705 were sequentially-injected with the RT57. Here, nearly 70% of the detected photons are above 610 nm and 60% occur within the Cy5.5 filter set (695-770 nm). Also, when the improvement in detectable photons is calculated, a similar increase in the number of photons detected is observed for all three filter sets for the in vivo (Table 3) and in vitro (Table 1) datasets when QD705 are present.

TABLE 4

Improvement of the photon transmission in a mouse thigh injection.

|  | QD705/Control |
|---|---|
| Open | 1.373 |
| 610LP | 3.839 |
| Cy5.5 | 10.773 |

Long Non-Conventional Excitation of QD705 from RT57

As RT57 luminescence caused QD705 emission under conditions in solution, where no covalent chemistry had been applied, this suggested that the mechanism of the detected phenomenon was not explained by BRET (a characteristically non-radiative) mechanism constrained by the criterion of intimate molecular proximity.

Figure 6:
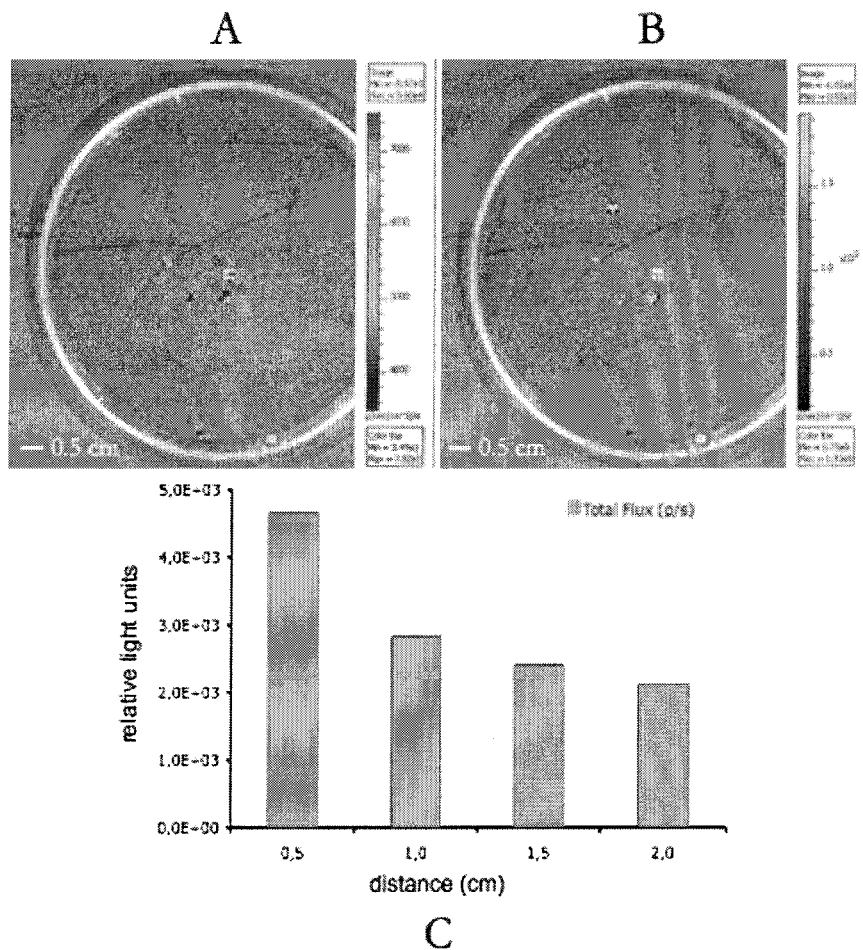
FIG. 6. Distance excitation of QD705 using RT57. An aliquot of stock RT57 was placed in the center of a Petri dish. Aliquots of QD705 were placed in increasing 0.5 cm intervals (center to center) from the RT57 up to a total working distance of 2 cm. (A) The resulting luminescence under the Cy5.5 filter set. (B) Verification of QD705 aliquot locations using fluorescence excitation. (C) Decreasing QD705 emission as a function of distance from the RT57.

Rather it raised the possibility that a radiative excitation-emission was responsible. To test this idea we next examined the ability of RT57 luminescence to excite aliquots of QD705 at macroscopic distances. In a series of experiments, we placed 5 µl stock RT57 onto the center of Petri dishes. Aliquots (2 µl) of QD705 were then placed onto the Petri dish, at increasing radial distances outward from the center, increasing at 5 mm increments to a total distance of 2 cm (i.e. distance between RT57 and QD705, center to center; FIG. 6A). The resulting luminescence was then observed for 300 s under the Cy5.5 filter set only due to its specificity to the QD705 emission, and the QD705 location verified using fluorescence imaging (FIG. 6B). As can be seen the intensity of the subsequent QD705 emission decreased as a function of distance from the bioluminescent RT57. However, the emission of the QD705 was readily detected up to a distance of 2 cm (FIG. 6C).

Use of FUEL to Enhance Signal Detection In Vivo

Bioluminescent *E. coli* bacteria suspended in a 50 µL bead of solidified 2% agarose were subcutaneously implanted into the inner left thigh of a BALB/c mouse. Another 50 µL bead of bacteria in agarose was prepared and coated with a layer of 10 µL quantum dots having an emission wavelength in the red at 705 nm. This second bead was subcutaneously implanted into the same mouse's inner right thigh.

Figure 10:
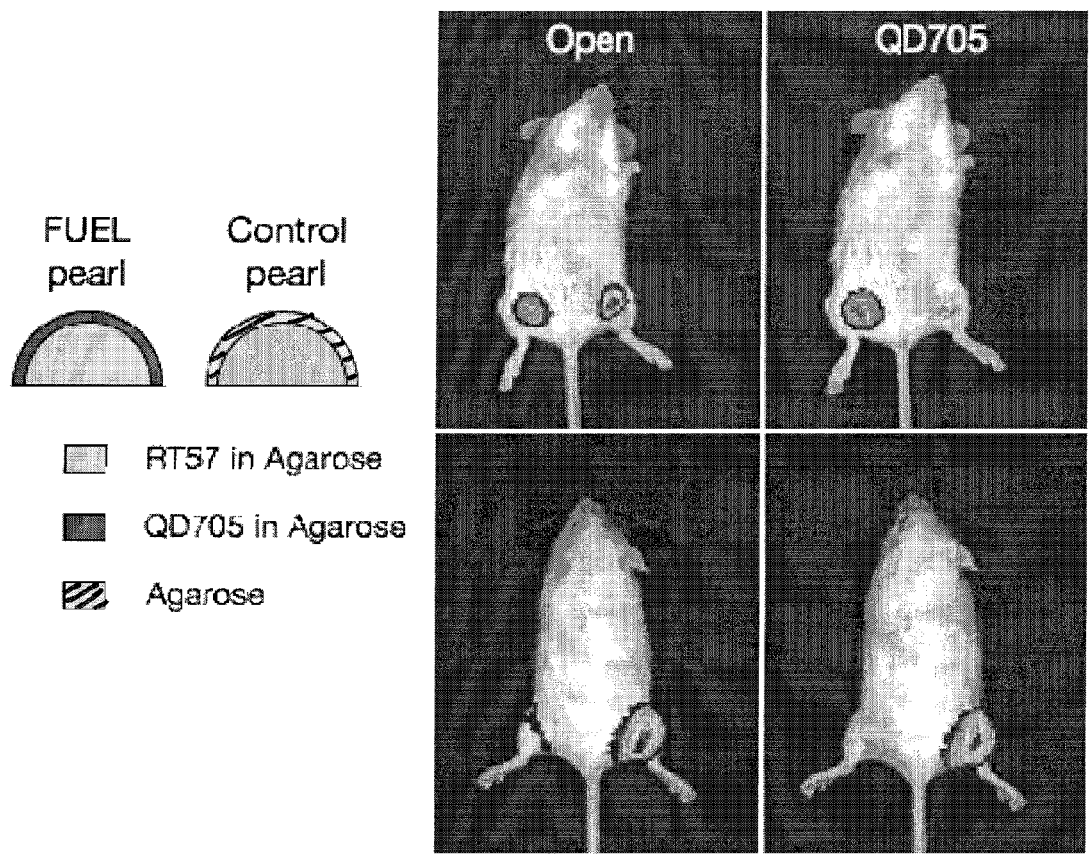
FIG. 10. In vivo demonstration of FUEL. Two different agar pearls were inserted subcutaneously into the left and right thigh of a female mouse. Each pearl consisted of an agarose+RT57 core. A second layer of either agarose or a mixture of QD705 in agarose was added to the pearl core, creating the Control or FUEL pearl, respectively. The mice were then placed into the imaging system and viewed ventrally and dorsally, through both the Open and QD705 filter sets. As can be seen, a limited red photon enhancement is observed when the mice are viewed ventrally under the Open filter set. Due to the presence of only a thin layer of skin, only a limited FUEL effect was expected. However, the FUEL effect is easily observed under the QD705 filter. The mice were then rotated such that any pearl luminescence had to pass through the entire mouse thigh before reaching the detector. In this case, the power of FUEL is easily observed in a significant increase in the total number of observed photons, in both the Open and QD705 filter sets.

When in the presence of the bacteria, the quantum dots are excited and shift the bioluminescent light from a wavelength of 480 nm to 705 nm. The 480 nm luminescence of the bacteria is visible from both legs without a filter in place (FIG. 10) and the intensities from both legs are nearly equivalent. When a Cy5.5 filter is applied (695-770 nm), the light from the bacteria is blocked from view and only the fluorescence from the excited quantum dots can be seen from the right thigh (FIG. 10).

The skin of the mouse is quite thin and readily traversable by light. However, when the mouse is turned over, emissions from the bacteria and quantum dots must cross the highly light-absorbing and scattering musculature of the leg before reaching the detector. Unlike the blue light from the bacteria, red light is not as susceptible to absorption by tissue chromophores like hemoglobin, oxyhemoglobin, melanin, lipids, and water. The shifted light from the quantum dot-containing bead in the right thigh is nearly four times more intense than the light coming from the bead with only bacteria in the left thigh when no filter is in place (FIG. 10). When the Cy5.5 filter is applied, the emission from the right leg is more than twenty-two times as great as that from the left leg (FIG. 10).

The FUEL Mechanism

The inventors have therefore shown that mixed in suspension bioluminescent bacteria are capable of exciting QDs due to the significant spectral overlap between the bioluminescent emission peak, with the broad absorption spectrum of the QD705, whereby the phenomenon is evidenced by the paradoxical red-shift of otherwise characteristically blue bacterial bioluminescence.

In as much as the same effect is qualitatively to be expected if this system were to be engineered so as to allow BRET to occur, this is certainly not the case under the conditions we described herein for the following reasons. First, the phenomenon occurs in suspension, in the absence of covalent chemistries, making it unlikely that the photonic moieties come into sufficiently close molecular proximity to achieve BRET. Second, the phenomenon is efficiently reproduced under conditions where moieties are physically separated by macroscopic distances, more characteristic of radiative excitation-emission.

Figure 11:
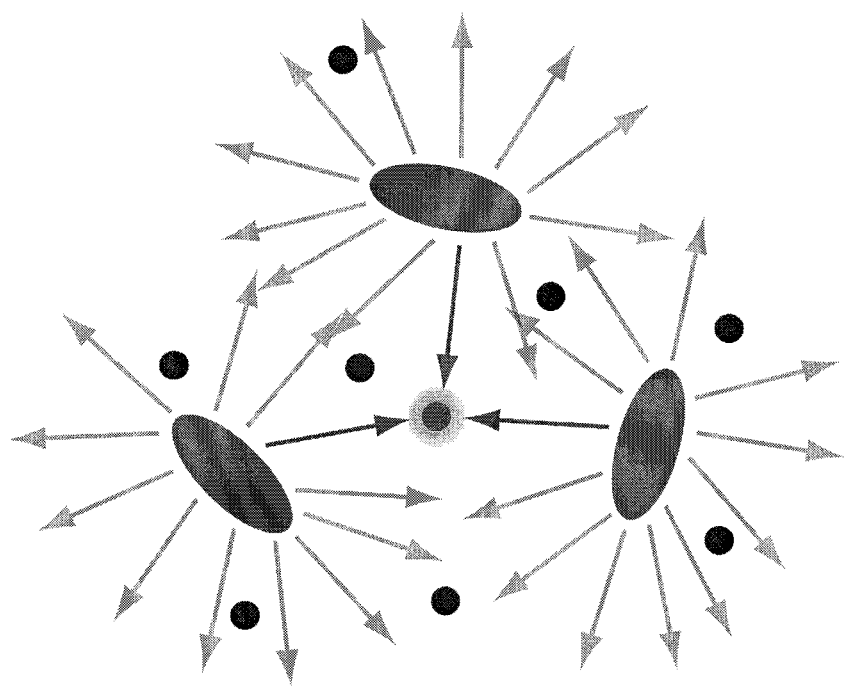
FIG. 11 A schematic representation of FUEL model In vivo. The bioluminescent *E. coli* radiate light in all directions. In the absence of QD705, some of the emitted photons will be absorbed by any quenchers (e.g. hemoglobin) that are present in vivo. When the QD705 are in proximity to the RT57, some of the emitted photons will be incident upon the QD705, inducing a fluorescent event which produces red-shifted photons which are poorly absorbed by the same quenchers. The increased production of red photons leads to an increased red luminescence signal and specificity for whole animal imaging.

The inventors have demonstrated that the FUEL effect can occur over distances of millimeters, inordinately further than could be achieved by any inter-molecular energy transfer process. It is interesting therefore that the resulting red-shift of the photon emission is strongly propagated through tissue prepared in vitro. In this case, the poor propagation of light from bacteria alone is due to a biophotonic behavior characteristic of blue light, i.e. high scatter and absorbance in tissue. By contrast, the inventors have shown that QD-based FUEL yields red luminescent photons through a Cy5.5 filter and have shown that it is this property that yields an order of magnitude enhancement of light detection in the presence of in vitro tissue since the red-shifted luminescence experiences minimal scatter and absorption compared to blue-green light. A schematic representation of FUEL is shown in FIG. 11.

The properties of FUEL therefore have the potential to be particularly advantageous for applications and for experiments and techniques performed in vivo such as bacterial dissemination or host-pathogen interactions and response. Perhaps surprisingly, it is clear that the presence of an optical absorber such as blood or tissue actually increases the specificity of FUEL inasmuch as the bioluminescent bacteria must be close to the QDs, but not necessarily within the molecular distance that would equate to BRET. The FUEL red-shifted photons are more able to pass through the blood and tissues, with the most significant enhancement in MWB.

Based upon the phenomenon and properties reported herein, FUEL has value particular application for experiments and techniques performed in vivo.

The Inventors have demonstrated the ability of bioluminescent E. coli to excite QDs at substantial distances, creating a red-shift in the detected photons through a process which they have termed FUEL. The photons are shifted away from the highly absorbing regions of hemoglobin (in its various forms) and tissues, to the optically transparent region of 700-900 nm. A significant increase in the number of detectable photons is observed when QD705 are present under ex vivo conditions.

Further, the inventors have shown FUEL to be distinct from BRET in as much as the working distances shown here are much greater (µm-cm) than accepted BRET conditions (<10 nm). Finally, the inventors have achieved a shift in the emitted photons without the use of any coupling chemistries.

FUEL could be used as a complimentary technique to BRET. Using BRET, one is able to observe specific protein interactions, which is a level of resolution that is not readily necessary for whole animal bioluminescence imaging. However, FUEL has a spatial resolution more on the scale of individual organs, which is more relevant to whole animal BLI. As such, the two techniques, while sharing similar principles, have vastly different applications and scales of operation. Furthermore, we suggest that the FUEL effect could be applied to in vivo settings.

REFERENCES

1. Contag, C. H.; Ross, B. D., It's not just about anatomy: in vivo bioluminescence imaging as an eyepiece into biology. *J Magn Reson Imaging* 2002, 16 (4), 378-87.
2. Troy, T.; Jekic-McMullen, D.; Sambucetti, L.; Rice, B., Quantitative comparison of the sensitivity of detection of fluorescent and bioluminescent reporters in animal models. *Molecular imaging: official journal of the Society for Molecular Imaging* 2004, 3 (1), 9-23.
3. Hutchens, M.; Luker, G. D., Applications of bioluminescence imaging to the study of infectious diseases. *Cell Microbiol* 2007, 9 (10), 2315-22.
4. Welsh, D. K.; Kay, S. A., Bioluminescence imaging in living organisms. *Curr Opin Biotechnol* 2005, 16 (1), 73-8.
5. Rogers, K. L.; Picaud, S.; Roncali, E.; Boisgard, R.; Colasante, C.; Stinnakre, J.; Tavitian, B.; Brûlet, P., Non-invasive in vivo imaging of calcium signaling in mice. *PLoS ONE* 2007, 2 (10), e974.
6. Curie, T.; Rogers, K. L.; Colasante, C.; Brûlet, P., Red-shifted aequorin-based bioluminescent reporters for in vivo imaging of Ca2 signaling. *Molecular Imaging* 2007, 6 (1), 30-42.
7. Wu, C.; Mino, K.; Akimoto, H.; Kawabata, M.; Nakamura, K.; Ozaki, M.; Ohmiya, Y., In vivo far-red luminescence imaging of a biomarker based on BRET from *Cypridina* bioluminescence to an organic dye. *Proc Natl Acad Sci USA* 2009, 106 (37), 15599-603.
8. So, M.; Xu, C.; Loening, A.; Gambhir, S.; Rao, J., Self-illuminating quantum dot conjugates for in vivo imaging. *Nature Biotechnology* 2006, 24 (3), 339-343.
9. Loening, A. M.; Dragulescu-Andrasi, A.; Gambhir, S. S., A red-shifted *Renilla* luciferase for transient reporter-gene expression. *Nat Meth* 2010, 7 (1), 5-6.
10. Colin, M.; Moritz, S.; Schneider, H.; Capeau, J.; Coutelle, C.; Brahimi-Horn, M. C., Haemoglobin interferes with the ex vivo luciferase luminescence assay: consequence for detection of luciferase reporter gene expression in vivo. *Gene Ther* 2000, 7 (15), 1333-6.
11. Branchini, B. R.; Ablamsky, D. M.; Davis, A. L.; Southworth, T. L.; Butler, B.; Fan, F.; Jathoul, A. P.; Pule, M. A., Red-emitting luciferases for bioluminescence reporter and imaging applications. *Analytical Biochemistry* 2010, 396 (2), 290-7.
12. Wu, P.; Brand, L., Resonance energy transfer: methods and applications. *Analytical Biochemistry* 1994, 218 (1), 1-13.
13. Pfleger, K. D.; Eidne, K. A., New technologies: bioluminescence resonance energy transfer (BRET) for the detection of real time interactions involving G-protein coupled receptors. *Pituitary* 2003, 6 (3), 141-51.
14. Takanishi, C. L.; Bykova, E. A.; Cheng, W.; Zheng, J., GFP-based FRET analysis in live cells. *Brain Res* 2006, 1091 (1), 132-9.
15. Dacres, H.; Wang, J.; Dumancic, M. M.; Trowell, S. C., Experimental determination of the Förster distance for two commonly used bioluminescent resonance energy transfer pairs. *Anal Chem* 2010, 82 (1), 432-5.
16. Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S., Quantum dots for live cells, in vivo imaging, and diagnostics. *Science* 2005, 307 (5709), 538-44.
17. Clapp, A. R.; Medintz, I. L.; Mauro, J. M.; Fisher, B. R.; Bawendi, M. G.; Mattoussi, H., Fluorescence resonance energy transfer between quantum dot donors and dye-labeled protein acceptors. *J Am Chem Soc* 2004, 126 (1), 301-10.
18. Bang, J. H.; Kamat, P. V., Quantum dot sensitized solar cells. A tale of two semiconductor nanocrystals: CdSe and CdTe. *ACS nano* 2009, 3 (6), 1467-76.
19. Reiss, P.; Bleuse, J.; Pron, A., Highly luminescent CdSe/ZnSe core/shell nanocrystals of low size dispersion. In *Nano Lett,* 2002; Vol. 2, pp 781-784.
20. Choi, K. H.; Schweizer, H. P., mini-Tn7 insertion in bacteria with single attTn7 sites: example *Pseudomonas aeruginosa. Nat. Protoc.* 2006, 1 (1), 170-178.
21. Rogers, K. L.; Martin, J. R.; Renaud, O.; Karplus, E.; Nicola, M. A.; Nguyen, M.; Picaud, S.; Shorte, S.; Ballet, P., Electron-multiplying charge-coupled detector-based bioluminescence recording of single-cell Ca2+. *J Biomed Opt* 2008, 13 (3), 031211.
22. Shu, X.; Royant, A.; Lin, M. Z.; Aguilera, T. A.; Lev-Ram, V.; Steinbach, P.; Tsien, R., Mammalian expression of infrared fluorescent proteins engineered from a bacterial phytochrome. *Science* 2009, 324 (5928), 804-7.
23. Yang, R.; Chang, L.; Wu, J.; Tsai, M.; Wang, H.; Kuo, Y.; Yeh, T.; Yang, C.; Lin, P., Persistent Tissue Kinetics and Redistribution of Nanoparticles, Quantum Dot 705, in Mice: ICP-MS Quantitative Assessment. *Environ. Health Perspect.* 2007, 5.
24. Hardman, R., A toxicologic review of quantum dots: toxicity depends on physicochemical and environmental factors. *Environ. Health Perspect.* 2006, 114 (2), 165-72.
25. Smith, A. M.; Duan, H.; Mohs, A. M.; Nie, S., Bioconjugated quantum dots for in vivo molecular and cellular imaging. *Adv Drug Deliv Rev* 2008, 60 (11), 1226-40.
26. Tsay, J. M.; Michalet, X., New light on quantum dot cytotoxicity. *Chemistry & Biology* 2005, 12 (11), 1159-61.
27. Cai, W.; Shin, D. W.; Chen, K.; Gheysens, O.; Cao, Q.; Wang, S. X.; Gambhir, S.; Chen, X., Peptide-labeled near-infrared quantum dots for imaging tumor vasculature in living subjects. *Nano Lett* 2006, 6 (4), 669-76.
28. Welsher, K.; Liu, Z.; Sherlock, S. P.; Robinson, J. T.; Chen, Z.; Daranciang, D.; Dai, H., A route to brightly fluorescent carbon nanotubes for near-infrared imaging in mice. *Nat Nanotechnol* 2009, 4 (11), 773-80.
29. Krueger, A., New carbon materials: biological applications of functionalized nanodiamond materials. *Chemistry* 2008, 14 (5), 1382-90.
30. Yu, S.-J.; Kang, M.-W.; Chang, H.-C.; Chen, K.-M.; Yu, Y.-C., Bright fluorescent nanodiamonds: no photobleaching and low cytotoxicity. *J Am Chem Soc* 2005, 127 (50), 17604-5.
31. Song, B.; Wang, G.; Tan, M.; Yuan, J., A europium(III) complex as an efficient singlet oxygen luminescence probe. *J Am Chem Soc* 2006, 128 (41), 13442-50.
32. Strovas, T. J.; Dragavon, J. M.; Hankins, T. J.; Callis, J. B.; Burgess, L. W.; Lidstrom, M., Measurement of respiration rates of *Methylobacterium extorquens* AM1 cultures by use of a phosphorescence-based sensor. *Appl Environ Microbiol* 2006, 72 (2), 1692-5.
33. Soini, A. E.; Seveus, L.; Meltola, N. J.; Papkovsky, D. B.; Soini, E., Phosphorescent metalloporphyrins as labels in time-resolved luminescence microscopy: effect of mounting on emission intensity. *Microsc Res Tech* 2002, 58 (2), 125-31.

The invention claimed is:

1. A method to determine the presence of a photon producing luminescent biological marker in a cell, tissue or organism of interest comprising the steps:
   a) providing conditions suitable for said biological marker to produce at least one first photon;
   b) providing a Fluorescence by unbound excitation luminescence Probe Pair-Upper (FPP-U), wherein said FPP-U is selected from the group consisting of quantum dots, carbon nanotubes, fluorescent proteins, diamond nanocrystals, and metalloporphyrins; and wherein said at least one first photon of step a) excites said FPP-U, which emits at least one second photon;
   c) detecting said at least one second photon;
   wherein said biological marker and said FPP-U are not bound and each of said at least one second photon is of a longer wavelength than each of said at least one first photon.

2. The method according to claim 1, wherein said biological marker is bioluminescent.

3. The method according to claim 1, wherein said biological marker is chemiluminescent.

4. The method according to claim 1, wherein said biological marker is fluorescent.

5. The method according to claim 1, wherein said biological marker emits photons with a wavelength of less than 650 nm.

6. The method according to claim 1, wherein said FPP-U emit photons with a wavelength of 650-900 nm.

7. The method according to claim 1, wherein said method comprises determining the presence of at least two photon producing biological markers in a cell, tissue or organism; wherein each of said at least two biological markers emits photons in a non-overlapping range of wavelengths which excite at least one of at least two subset of said FPP-U which each emits at least one photon, wherein said at least one photon emitted by each said subset of said FPP-U is in a non-overlapping range of wavelengths.

8. The method according to claim 1, wherein said FPP-U comprises a means to target it to a specific portions of said cell, tissue or organism.

9. The method according to claim 1, wherein said FPP-U is disposed inside said cell, tissue or organism.

10. The method of claim 1, wherein said FPP-U is disposed outside of said cell, tissue or organism.

11. The method of claim 1, wherein said FPP-U is disposed inside and outside of said cell, tissue or organism.

12. A method to determine the presence of a photon producing luminescent biological marker in a cell, tissue or organism of interest comprising the steps:
   a) providing conditions suitable for a first probe of a pair of probes for Fluorescence by unbound Excitation from Luminescence, named FPP, to produce at least one first photon;
   b) providing a second FPP disposed in proximity to said cell, tissue or organism, wherein said at least one first photon of step a) excites said second FPP, which emits at least one second photon;
   wherein step b) is repeated at least one further time, wherein for each additional step a further FPP is disposed in proximity to said cell, tissue or organism, other than said first or second FPP, which is specifically excited by the at least one photon emitted in the previous step and which in turns emits at least one further photon;
   wherein in a final step said at least one further photon is detected;
   wherein said biological marker is either said first or said second FPP;
   wherein said plurality of FPPs are not bound and in that each of said at least one photon (s) are of a longer wavelength than each of said at least one photon (s) from the previous step.

* * * * *